(12) United States Patent
Kim et al.

(10) Patent No.: US 7,697,032 B2
(45) Date of Patent: Apr. 13, 2010

(54) INTEGRATED CHIP FOR DETECTING EYE MOVEMENT

(75) Inventors: Dongsoo Kim, Seoul (KR); Gunhee Han, Gyunggi-do (KR); Jae Hoon Song, Great Falls, VA (US)

(73) Assignee: MIRU Enterprise, Inc., Vienna, VA (US)

( * ) Notice: Subject to any disclaimer, the term of this patent is extended or adjusted under 35 U.S.C. 154(b) by 1090 days.

(21) Appl. No.: 11/332,489

(22) Filed: Jan. 17, 2006

(65) Prior Publication Data

US 2007/0013652 A1 Jan. 18, 2007

(51) Int. Cl.
*H04N 5/225* (2006.01)

(52) U.S. Cl. .................... 348/207.99; 348/144; 382/103

(58) Field of Classification Search ................. 345/156, 345/157; 382/103; 348/308, 207.99, 144–146; 600/558
See application file for complete search history.

(56) References Cited

U.S. PATENT DOCUMENTS 5,481,622 A * 1/1996 Gerhardt et al. ............. 382/103
6,120,461 A * 9/2000 Smyth ........................ 600/558
6,515,702 B1 2/2003 Yadid-Pecht et al.
2003/0218678 A1 11/2003 Lin et al.

FOREIGN PATENT DOCUMENTS

| JP | 2000-163015 | 6/2000 |
|----|-------------|---------|
| JP | 2001-339643 | 12/2001 |
| JP | 2002-150293 | 5/2002 |
| WO | WO 03/053043 A1 | 6/2003 |

* cited by examiner

*Primary Examiner*—Tuan Ho
(74) *Attorney, Agent, or Firm*—Hunton & Williams, LLP (57) ABSTRACT

According to one embodiment, the present invention relates to an integrated chip for detecting eye movement. An eye tracker device may include a CMOS image sensor which provides an imaging process of a user's eye image. The eye tracker device may be implemented on a single chip where pixel-level image processing is performed, thereby achieving high operating speed. A smart CMOS Image Sensor (CIS) pixel array may include a CMOS image sensor with a "shrink" function of locating a center of a pupil while eliminating influence of a black region around the eyebrow or pupil at the pixel level so as to accurately find the location at which a user views. The CIS pixel array may include an "expand" function of removing glint or other interference occurring in the pupil due to external light or other source.

30 Claims, 9 Drawing Sheets

INTEGRATED CHIP FOR DETECTING EYE MOVEMENT

CROSS-REFERENCE TO RELATED APPLICATIONS

This patent application claims priority to Korean Patent Application No. 10-2005-0064188, filed Jul. 15, 2005 and PCT application PCT/KR2005/002610 filed Oct. 11, 2005, which are hereby incorporated by reference herein in their entirety.

FIELD OF THE INVENTION

The present invention relates generally to an eye tracker device for detecting eye movement and, more particularly, to an integrated chip for detecting eye movement where imaging processing is performed at a pixel level thereby providing high operating speed.

BACKGROUND OF THE INVENTION

Figure 1:
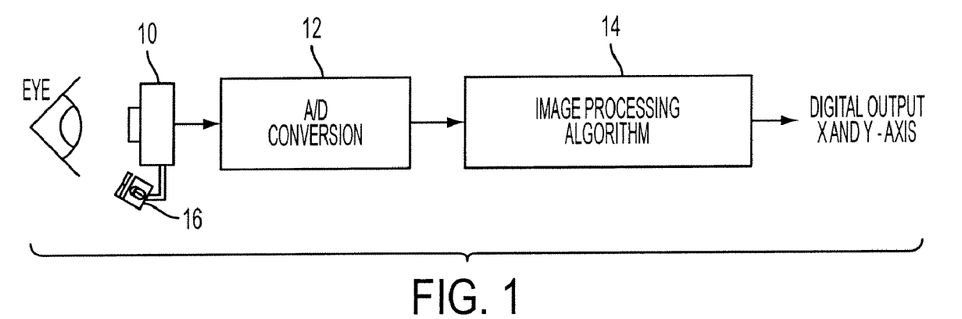
FIG. 1 is a block diagram illustrating a traditional eye tracker according to the prior art.

An eye tracker refers to a device that detects coordinates of a position that a user is viewing where the coordinates are output as digital data. This device may be known as an advanced-level Human-Computer Interface (HCI), such as a Head Mounted Display (HMD). Traditional eye tracker devices require several peripheral devices, such as a camera 10 with a charge coupled device (CCD) image sensor, an A/D converter 12, and a DSP chip 14 with an image processing algorithm therein, as shown in FIG. 1. In the traditional system, a user's eyes are irradiated with infrared rays 16 where images of the user's eyes are obtained by camera 10 and further processed.

In the traditional system, the eye's images obtained through the CCD camera 10 are applied to A/D converter 12 which converts the images into a digital signal. Thereafter, the converted digital signal is applied to digital signal processing (DSP) chip 14 (or a microprocessor) which in turn finds a center of the pupil of each eye through the image processing algorithm based on the digital signal.

The traditional eye tracker system, however, requires several peripheral devices resulting in an increase in component cost and printed circuit board (PCB) fabrication cost. Further, the CCD and the DSP chip consume a large amount of power and are difficult to miniaturize. In addition, a long delay is required to identify a center of the pupil of the eye due to the limited performance of the traditional DSP chip and the image processing algorithm.

In view of the foregoing, it would be desirable to provide an integrated chip for detecting eye movement.

SUMMARY OF THE INVENTION

According to an exemplary embodiment of the present invention, an integrated chip for detecting eye movement comprises a sensor component for receiving an image of a user's eye and processing the eye image to identify a center of a pupil of the eye image; wherein the sensor component comprises a CMOS image sensor (CIS) pixel array, wherein the CIS pixel array comprises: a shrink means for reducing a dark interference region around a pupil portion of the eye's image; and an expand means for reducing a light interference region occurring in the pupil portion of the eye's image, wherein the CIS pixel array identifies a center of the pupil of the eye image at a pixel level where the center of the pupil identifies a point the user is viewing.

In accordance with other aspects of this exemplary embodiment of the present invention, the shrink means reduces the dark interference region by converting a plurality of dark pixels of the dark interference region to a plurality of white pixels; the expand means reduces the light interference region caused by a light source or external source; the CIS pixel array comprises a M×N cellular neural network having M columns and N rows, where each pixel of the CIS pixel array outputs a current state value where each corresponding current state value for each pixel is summed for a plurality of rows and columns; the each pixel of the CIS pixel array comprises a photodiode, where an output voltage of the photodiode is changed depending on brightness of light; a plurality of winner-take-all (WTA) circuits connected to a plurality of rows and columns of the CIS pixel array for identifying a location of a row and a column having a highest current value in the row and column and generating an output signal indicative of the identified location and a plurality of loadable shift registers (LSRs) connected to the plurality of WTA circuits for receiving the output signal, storing the received output signal and outputting the stored output signal through a shift operation; a plurality of winner-take-all (WTA) circuits connected to a plurality of rows and columns of the CIS pixel array for identifying a location of a row and a column having a highest current value and generating an output signal indicative of identified location; and a plurality of encoders connected to the plurality of WTA circuits for receiving the output signal to encode the received output signal and outputting the encoded signal; a stop criterion circuit connected to the plurality of WTA circuits and the plurality of LSRs for receiving the output signal and generating a LSR latch signal so that when a number of black pixels of the row and column of the CIS pixel array is less than a predetermined number, the location of the row and column is stored in the LSR; the predetermined number of the black pixels is two; the stop criterion circuit compares a highest current value $I_{WIN,h}$ and $I_{WIN,v}$ of the input signals of the row and column with a reference current value $I_{STOP}$, and generates a latching signal for application to the LSRs if $I_{WIN,h}$ and $I_{WIN,V}$ are lower than $I_{STOP}$, respectively, wherein the LSRs outputs digital data.

In accordance with other aspects of this exemplary embodiment of the present invention, a system comprises the integrated chip described above, wherein the integrated chip is in communication with a receiving device configured to receive an output from the integrated chip for identifying the point the user is viewing on the receiving device; wherein the point the user is viewing is a target in a training simulator; wherein the training simulator identifies the target viewed by the user and an actual target of the training simulator and wherein the target viewed by the user and the actual target are compared; wherein the point the user is viewing is a target in an interactive game application; wherein a direction that the receiving device is positioned is controlled by the output; wherein an action of the receiving device is further controlled by another output of the integrated chip; wherein one or more characteristics of the eye image are determined; wherein the user's identity is determined by the one or more characteristics of the eye image; wherein the receiving device is a laser device used in eye laser surgery wherein the laser device is configured to avoid a predetermined area of the eye; wherein the receiving device is a transportation device that is configured to receive the point the user is viewing as input to control the transportation device; wherein the transportation device is one of a vehicle and a wheelchair; wherein the point the user is viewing identifies a security code for entry to the receiving device; wherein the receiving device is an automated teller machine; wherein the point the user is viewing is received as input to a component within a vehicle; wherein the component within the vehicle is a global positioning system; and wherein the integrated chip is connected to an eye piece positioned at a close proximity to a user's eye area.

According to an exemplary embodiment of the present invention, a method for implementing an integrated chip for detecting eye movement, wherein the integrated chip comprises an image sensor component for receiving an eye image and processing the eye image to identify a center of a pupil of the eye, comprises the steps of receiving an eye image by the image sensor; identifying an interference in the eye image; removing the interference in the eye image, wherein the step of removing interference comprises at least one of a shrink function for removing a dark interference region around the pupil of the eye image by modifying a plurality of dark pixels into white pixels and an expand function for removing a light interference region in the pupil of the eye image; and locating a center of a pupil of the eye image at a pixel level where the center of the pupil identifies a point the user is viewing.

In accordance with other aspects of this exemplary embodiment of the present invention, the method further comprises outputting a current state value of each pixel of a CIS pixel array that corresponds to one or more of light and shade wherein the corresponding current values are summed for the rows and columns of the CIS pixel array; identifying a location of row and column having a highest current value in the CIS pixel array and outputting a signal indicative of the location of the row and column to a receiving device; wherein the step of outputting further comprises the steps of comparing the highest current value $I_{WTN,h}$ and $I_{WTN,V}$ of input signals of the row and column with a reference current value $I_{STOP}$; and generating digital data as an output if $I_{WTN,h}$ and $I_{WTN,V}$ are lower than $I_{STOP}$.

BRIEF DESCRIPTION OF THE DRAWINGS

In order to facilitate a fuller understanding of the present inventions, reference is now made to the appended drawings. These drawings should not be construed as limiting the present inventions, but are intended to be exemplary only.

DETAILED DESCRIPTION OF EXEMPLARY EMBODIMENT(S)

An embodiment of the present invention generally relates to providing an eye tracker device using an image sensor (e.g., a CMOS image sensor) for processing an image of a user's eye. The eye tracker of an embodiment of the present invention may be implemented using a single chip where pixel-level image processing may be performed thereby ensuring high operating speed.

An eye tracker device of an embodiment of the present invention may operate in various modes. An exemplary first mode detects a location that a user is viewing by accurately finding a center of a pupil of the user's eye. An exemplary second mode converts the eye's images, which may be obtained by an image sensor (e.g., CMOS image sensor), into a digital signal, which may be performed through a Correlated Double Sampling (CDS) circuit and an A/D converter. Other components providing similar functionality may be implemented as well.

A smart CMOS Image Sensor (CIS) pixel array ("CIS pixel array") may accurately identify a center of a pupil while eliminating or minimizing interference. For example, an image sensor, such as a CMOS image sensor, may include a "shrink" function and an "expand" function for eliminating or minimizing interference around the pupil and/or in the pupil of the eye image. For example, the "shrink" function may eliminate or minimize a dark interference region around the eyebrow or pupil. The dark interference region may be caused by an eyelash, eyebrows, dust, particles and/or other interference that may appear as a "dark" region. For example, an eyebrow region or eyelashes may reflect a dark or black region that may interfere with the process of identifying the center of the pupil. Other factors, such as dust or other particles, may also interfere with the process. By processing the dark interference region at the pixel level, an embodiment of the present invention can accurately identify a center of the pupil and thereby accurately identify the location a user is viewing.

In addition, the CIS pixel array may include an "expand" function for removing glint or other interference that may reflect onto the pupil from an external source, such as external light (e.g., indoor lighting), reflection or other interference. By addressing the various interferences, an embodiment of the present invention achieves higher accuracy and overall improvement in system performance.

For example, a "shrink" function may refer to an operation in which the size of the black or dark region around the eyebrow and/or pupil is reduced as the edges of the black or dark region are gradually changed to white or light pixels. In another example, the "expand" function may refer to an operation in which the white or light region is filled with black or dark regions. The image processing steps of the embodiments of the present inventions involve extensive calculation, but can be completed within several tens of µsec through the pixel-level interaction.

For the inventive CIS of an embodiment of the present invention, a standard CMOS process may be employed for fabrication of the CIS so that circuit integration for processing an analog signal, a digital signal and a mixed signal may be achieved as well as implementation of the inventive CIS on a single chip. Accordingly, the manufacturing cost is reduced, thereby resulting in cost efficiencies. Since a reasonably priced eye tracker device may be realized, HCI such as an advanced-level HMD may be commercialized to a wide range of users for various different applications. In addition, the CIS pixel array of an embodiment of the present invention may be used to locate a center of the pupil of an eye as well as reducing the time involved in the image processing process. The CIS pixel array may implement an iris recognition system and/or other recognition systems (e.g., a fingerprint recognition system, etc.) within a single chip for a wide variety of applications.

Figure 2:
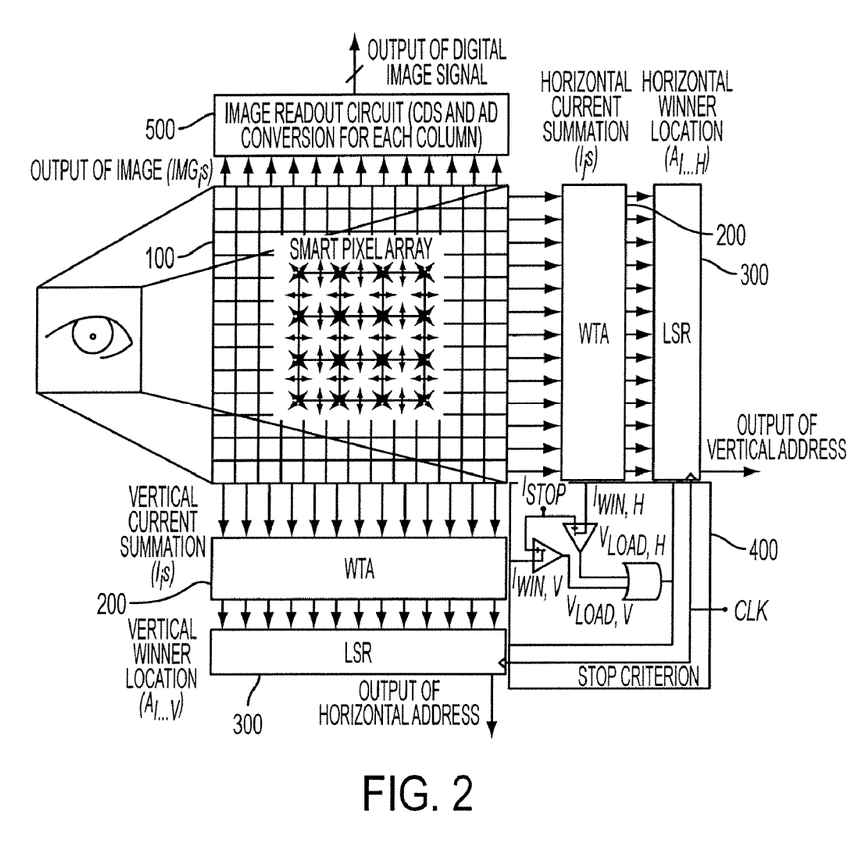
FIG. 2 is an exemplary diagram illustrating an integrated eye tracker, according to an embodiment of the present invention.

Referring to FIG. 2, an eye tracker according to an embodiment of the present invention may include a smart CIS pixel array 100, a Winner-Take-All (WTA) circuit 200, a Loadable Shift Register (LSR) 300, a stop criterion circuit 400 and an image readout circuit 500. While separate components are shown, the components may be combined and/or further separated or replicated within the various embodiments of the present inventions. In addition, other components that provide similar or equivalent functionality may be implemented.

Figure 3:
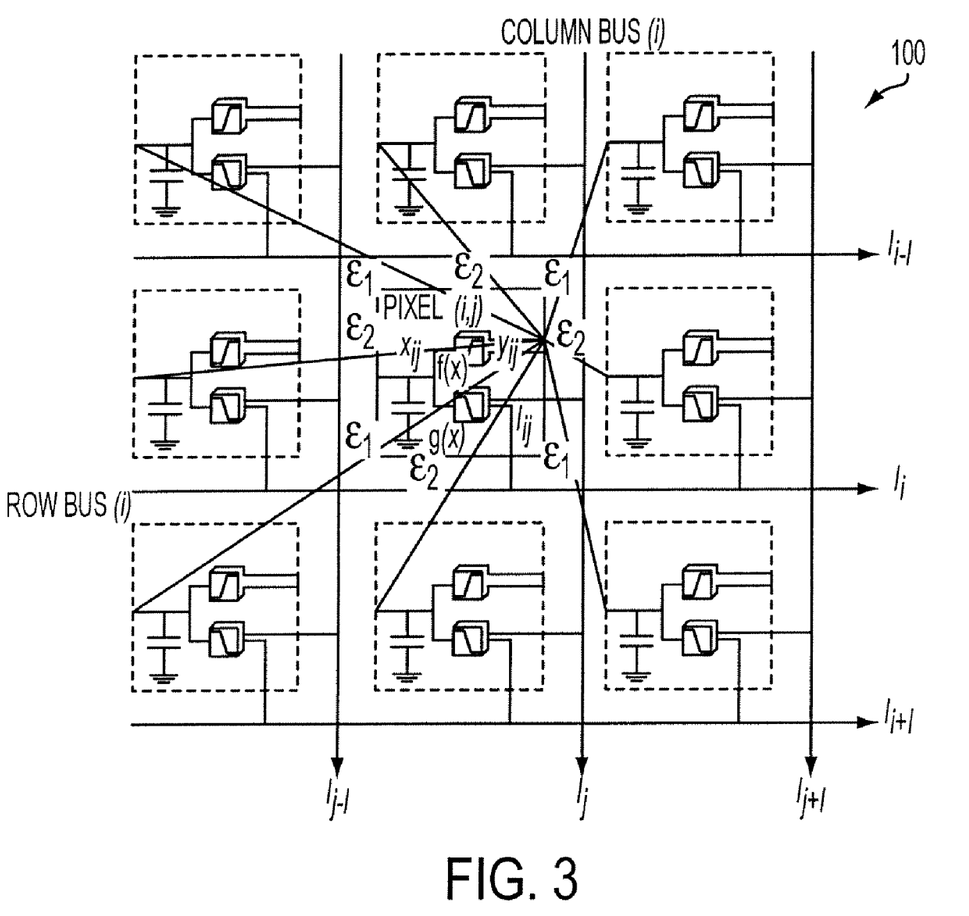
FIG. 3 is an exemplary diagram of a smart CIS pixel array, according to an embodiment of the present invention.

FIG. 3 illustrates a block diagram of a smart CIS pixel array 100, according to an embodiment of the present invention. The smart CIS pixel array 100 may be modeled into a M×N cellular neural network having M columns and N rows. Assuming that a pixel (e.g., central pixel of FIG. 3) is positioned in an $i^{th}$ row and a $j^{th}$ column is C(i,j), pixels $N_1$(i,j), $N_2$(i,j) around C(i,j) may be expressed in the following Equation:

$$N_1(i,j)=[C(i-1,j-1),C(i-1,j+1),C(i+1,j-1),C(i+1,j+1)]$$

$$N_2(i,j)=[C(i-1,j),C(i,j-1),C(i,j+1),C(i+1,j)]$$

further, assuming that u(i,j), x(i,j), y(i,j) are input, state, output of C(i,j), respectively, x(i,j) and y(i,j) may be expressed in the following Equation:

$$\begin{cases} \dfrac{dx(i,j)}{dt} = \dfrac{du(i,j)}{dt} + \sum_{C(k,l) \in N_1(i,j)} \varepsilon_1 y(k,l) + \sum_{C(k,l) \in N_2(i,j)} \varepsilon_2 y(k,l) \\ y(i,j) = f(x(i,j)) \end{cases}$$

where $\varepsilon_1$, $\varepsilon_2$ are feedback gain coefficients and f(.) is a saturation function.

For example, if y(i,j) has a value higher than a predetermined reference value when $\varepsilon_1$, $\varepsilon_2$ are in the range of $0<\varepsilon_1<\varepsilon_2<1$, a positive feedback may be applied to the pixels around C(i,j). On the other hand, if y(i,j) has a value lower than a predetermined reference value, a negative feedback may be applied to the pixels around C(i,j). The pixels perform the "shrink" function while being closely interconnected to one another. In the "shrink" function, when a corresponding pixel itself takes a white portion of an eye's image, the positive feedback may be applied to black pixels around the corresponding pixel of the white portion so that the black pixels are changed to white pixels. In this manner, while the size of the black region of the pixels shrinks, the "shrink" function is performed (shrink1 function of FIG. 5).

Figure 5:
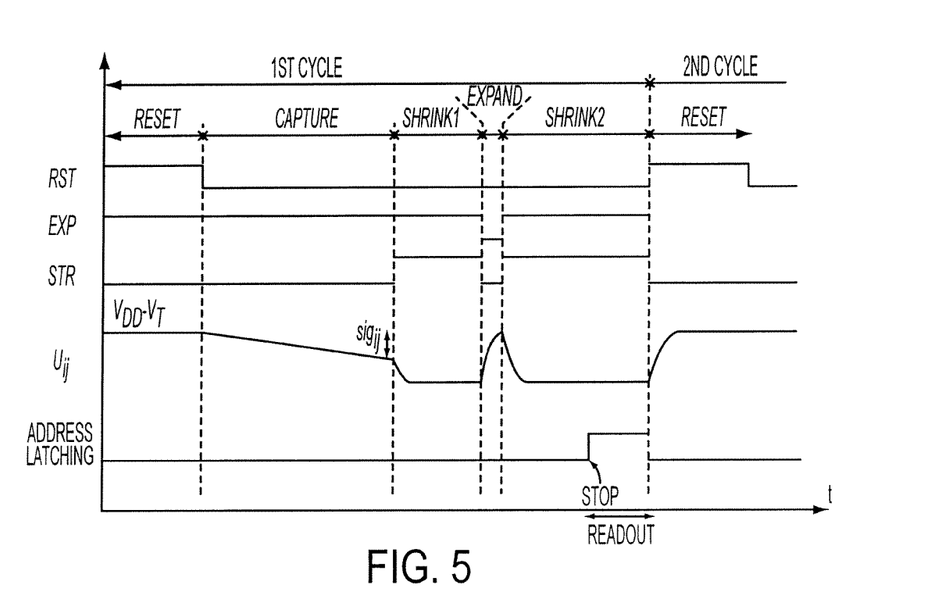
FIG. 5 is an exemplary signal timing diagram of a smart CIS pixel array, according to an embodiment of the present invention.

If y(i,j) has a lower value than the predetermined reference value, the black region of the image pixel may be widened during the "expand" function by a negative feedback (expand function of FIG. 5). Referring to the images of the eye(s), an image of an interference (e.g., eyelashes) as indicated by multiple black (or dark) dots will disappear while repeatedly performing the shrink function. Ultimately, only the black region of the pupil will remain and shrink gradually. In the case where a white (or light) glint or other interference due to external light (or other source) is generated in the black region of the pupil, an error in finding the center of the pupil in this region may occur. To obviate such an error, the white glint region or light region may be filled with a black or dark region through the "expand" function and then the "shrink" function may be performed (shrink2 function of FIG. 5).

Figure 4:
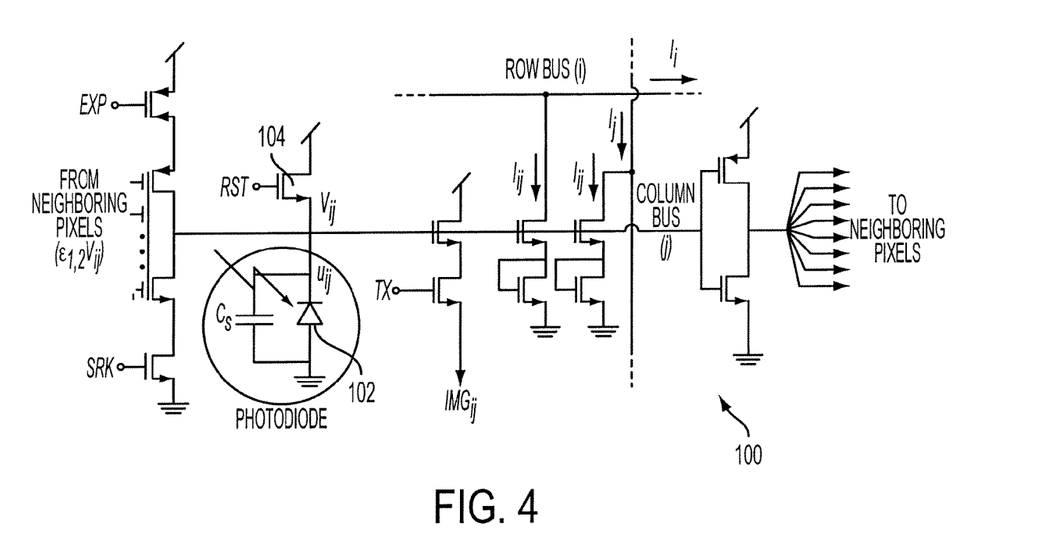
FIG. 4 is an exemplary circuit diagram of a smart CIS pixel array, according to an embodiment of the present invention.

FIGS. 4 and 5 illustrate an exemplary circuit diagram and an exemplary timing diagram of a smart CIS pixel array 100, according to an embodiment of the present invention. Referring to FIGS. 4 and 5, a photodiode 102 may be pre-charged in a first reset step. Then, while a RST transistor 104 is turned off, an output voltage of the photodiode 102 may be changed depending on the brightness of light in a capture step. Subsequently, the center of the pupil may be identified through the shrink1 step, the expand step and the shrink2 step as mentioned above. Depending on the type of interference, additional shrink and/or expand steps may also be implemented. In addition, a single shrink step may be implemented. Other variations may be realized in response to the interference identified.

Figure 6:
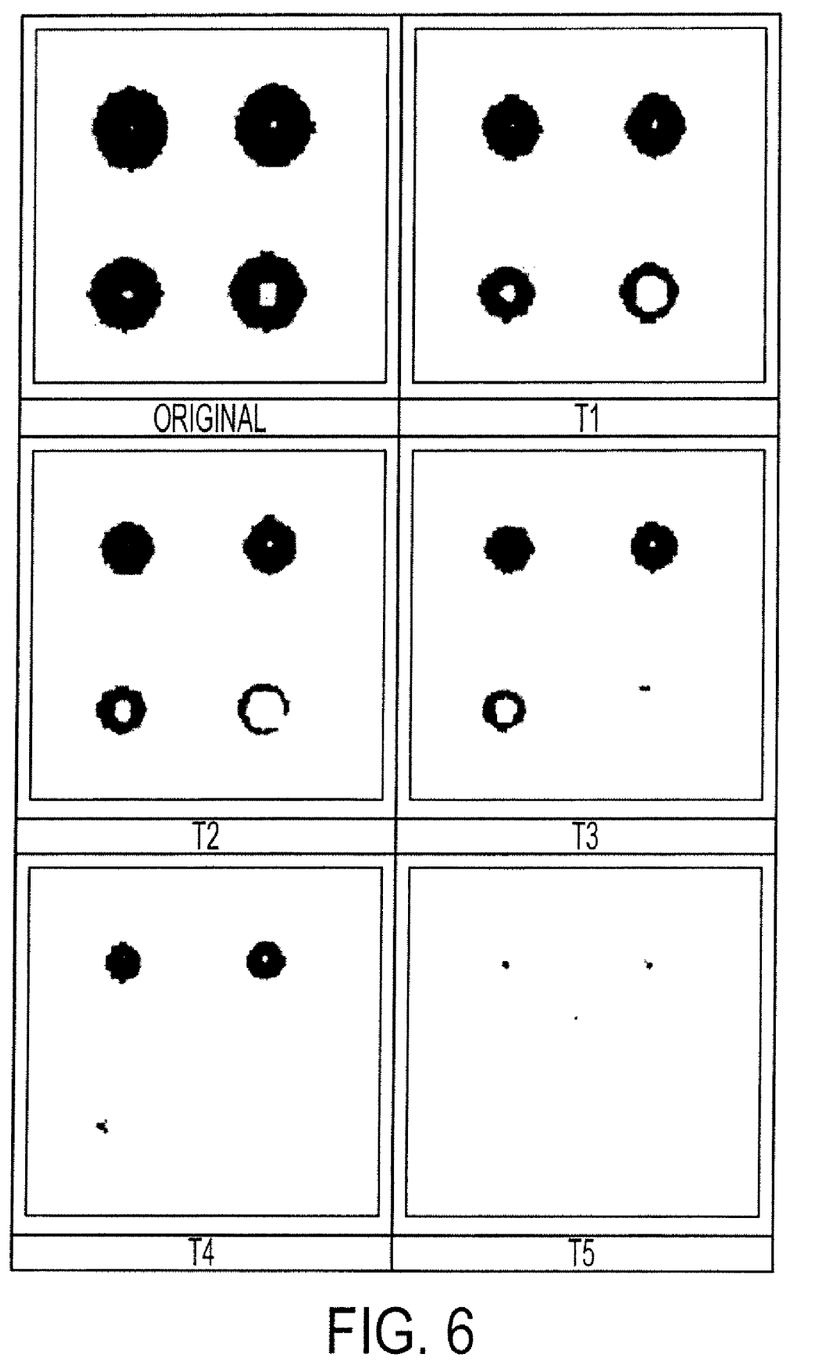
FIG. 6 shows an exemplary screen for illustrating an influence of a shrink function depending on a glint amount, according to an embodiment of the present invention.

FIG. 6 illustrates a screen for illustrating influence of a "shrink" function depending on a glint amount, according to an embodiment of the present invention. Referring to FIG. 6, that the shrink function is performed in order to find the center of the pupil may mean that a positive feedback is applied to black pixels around a corresponding pixel so that the black pixels become white pixels. In the case where the corresponding pixel takes a black region, the edge of the black pixel first starts to change to white pixels and the black region is shrunk as it goes toward the center of the pupil. If the white region exists within the black region again, however, this white region may be either enlarged, or shrunk toward the center. In this case, an error may be generated. Thus, if the "expand" function is performed after eliminating the influence of the black region around the pupil by initially performing the "shrink" function, the black region may be gradually enlarged and then the shrink function may be performed again after removing glint or other interference. As shown in FIG. 6, in the case where glint (or other light interference) exists in the black region of the pupil, there is an influence depending on the amount of glint when the shrink function is performed.

The WTA circuit 200 may identify the location of the row and the column that has the greatest number of black pixels and convey the number of black pixels in the row and column to the LSR 300 and the stop criterion circuit 400. The stop criterion circuit 400 may generate a LSR latch signal so that when the number of black pixels of the row and column of the CIS pixel array is less than a predetermined number (e.g., 2 or less) at the center of the pupil, the location of the row and column can be stored in the LSR 300. The above operation process is shown in FIG. 7.

The operation of an embodiment of the present invention will be described below with reference to FIGS. 7 and 8. At the initial state (reset), the eye's images may be received by an image sensor (capture), at step 10. The smart CIS pixel array 100 may remove a black or dark interference region in the area around the pupil by changing the black region into white pixels through a "shrink" function, and may remove a light interference region, such as glint or other interference that occurs in the pupil through an "expand" function. The CIS pixel array may then reduce the black or dark interference region through the "shrink" function, at step 20. Each pixel of the CIS pixel array 100 may output its own state, e.g., a current value corresponding to light and shade. The corresponding current values may then be summed for each row and/or column, as shown in FIG. 3.

Figure 7:
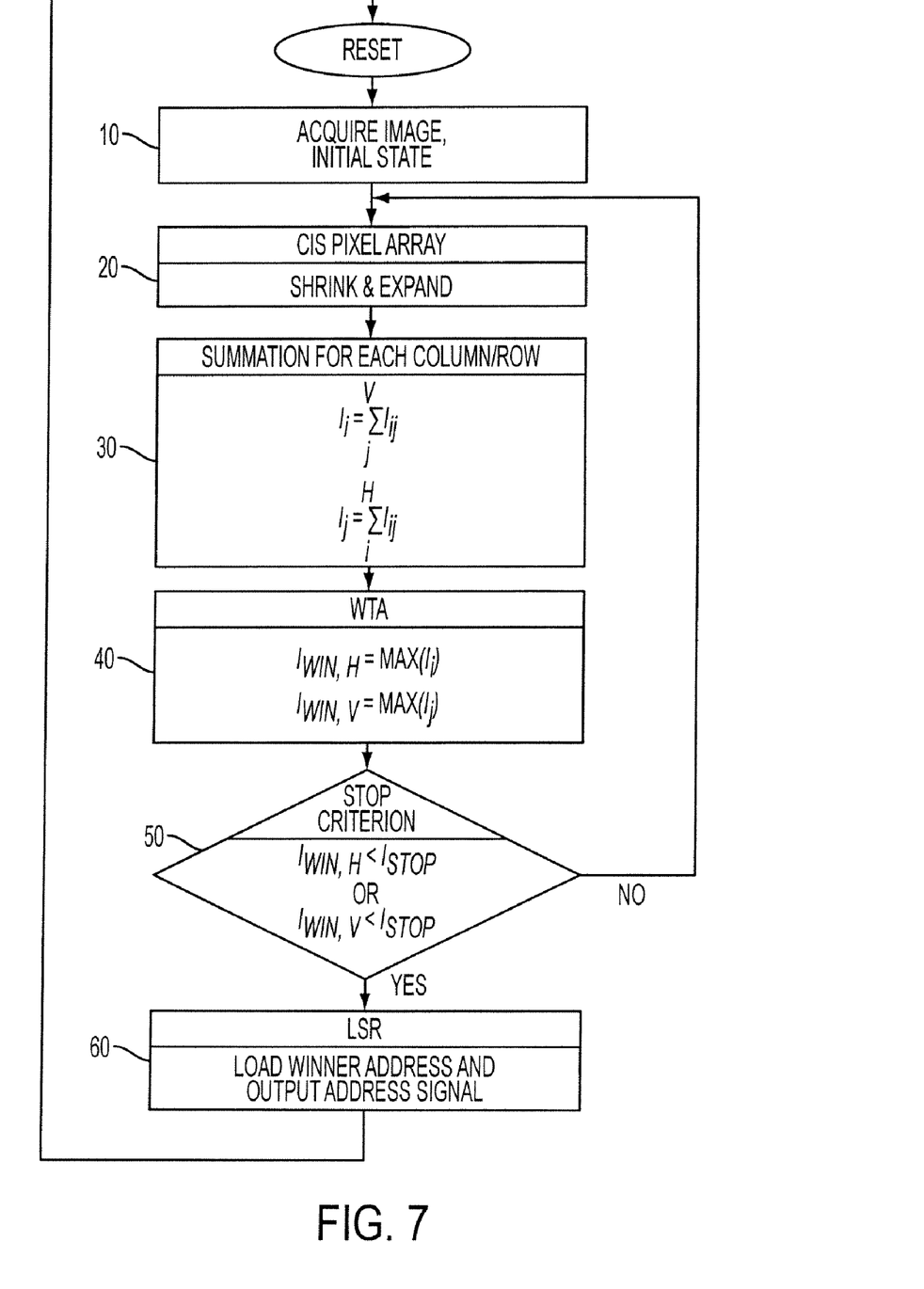
FIG. 7 is an exemplary flowchart for illustrating an eye tracking function, according to an embodiment of the present invention.

The WTA 200 may identify the location of a row (and/or column) having the highest current value in each row (and/or column) of the CIS pixel array one by one, e.g., the location of a row (and/or column) having a greatest number of black pixels, and may apply an output signal indicating the identified location to the LSR 300, as shown by steps 30 and 40 and with further reference to FIGS. 2 and 7. The stop criterion circuit 400 may forward an address signal indicating the location of a row and column (e.g., a winner) to the LSR 300 when the number of black pixels of the row and column is less than a predetermined number (e.g., 2 or less), at step 50. The LSR may then output the address signal, at step 60.

Figure 8:
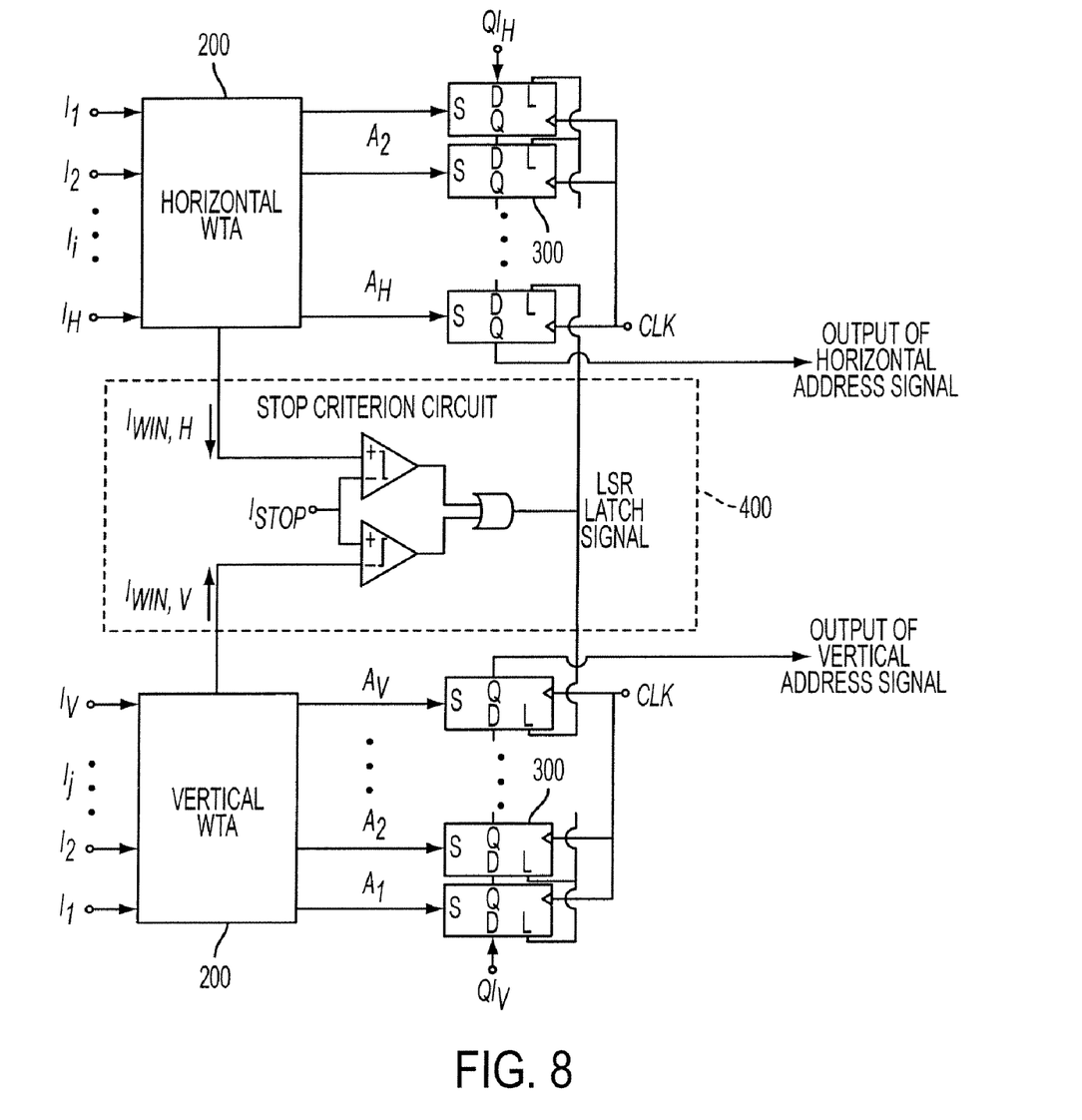
FIG. 8 is an exemplary diagram illustrating WTA, LSR and stop criterion circuits, according to an embodiment of the present invention.

For example, as in FIG. 8, the stop criterion circuit 400 may compare the highest current value $I_{WIN,h}$ and $I_{WIN,v}$ of the input signals of the row and column with a reference current value $I_{STOP}$, and generate a latching signal for application to the LSR 300 if $I_{WIN,h}$ and $I_{WIN,v}$ are lower than $I_{STOP}$, respectively, so that data may be transmitted from the row and column WTA 200 to each LSR 300. Therefore, the LSR may generate digital data as a final output. The image sensor may receive a subsequent image, at step 10, so that the above procedure may be repeatedly performed in order to find the center of a new pupil.

Figure 9:
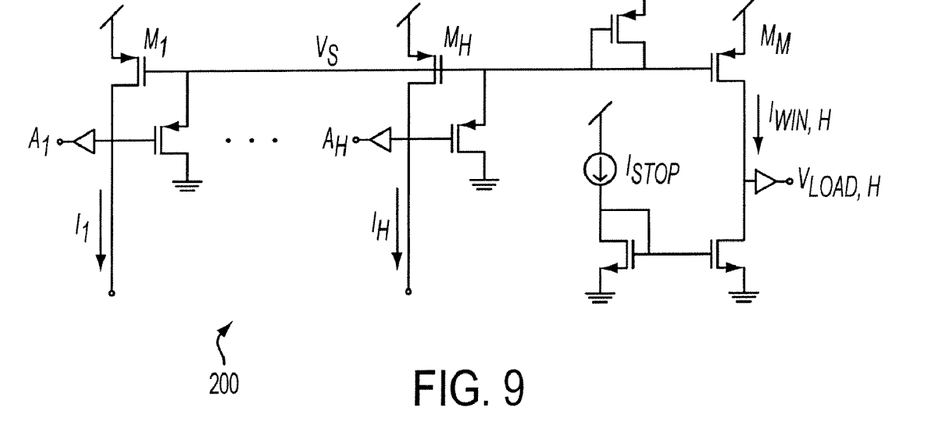
FIG. 9 is an exemplary circuit diagram of a WTA circuit, according to an embodiment of the present invention.

FIG. 9 illustrates an example of a circuit diagram of the WTA circuit 200, according to an embodiment of the present invention. For the WTA, a voltage Vs may be set such that the highest current value of $I_1, \ldots, I_H$ may be copied as $I_{WIN,H}$. In addition, only one of $A_1, \ldots, A_H$ which has the highest current value has a high level value and the remaining ones have a low level value. An address load signal may be generated based on a comparison of $I_{WIN,H}$ and $I_{STOP}$ current.

Before black dots are changed to white dots through the above operation, they may be input to the LSR 300 by the stop criterion circuit 400 (load). The relationship between the WTA 200, the stop criterion circuit 400 and the LSR 300 in FIG. 8 will be described below in more detail. $I_1, \ldots, I_H$ indicates the sum of pixel currents in each row and $I_1, \ldots, I_V$ indicates the sum of pixel currents in each column.

The WTA 200 may identify a row and column having the highest current from the input current and finds the number of black pixels of the row and column. If the shrink function is performed, the size of the black region is reduced and the values of $I_{WIN,H}$ and $I_{WIN,V}$ are also gradually reduced accordingly. The stop criterion circuit 400 may generate an address load signal (e.g., a latch signal) if the current $I_{WIN,H}$ and $I_{WIN,V}$ are less than a current corresponding to the case where the number of black pixels is two (or other predetermined value). As a result, the LSR 300 outputs the address signal.

According to an embodiment of the present invention, a pixel may refer to a pixel that performs the "shrink" and "expand" functions on surrounding pixels at a pixel level. Therefore, the method of an embodiment of the present invention may be performed efficiently. Furthermore, the WTA or the stop criterion circuit may send the location of an image to an output. The smart pixel of an embodiment of the present invention may send an image and also perform a function of obviating the influence around the eyes through the "shrink" and/or "expand" (e.g., removal of interference) function and accurately finding the center of the pupil. In addition, the inventive smart pixel may track the location at which a user views using the WTA, the stop criterion circuit and the LSR through the interaction between and/or among these pixels.

According to the embodiments of the present invention, other variations in circuitry may be implemented. For example, an embodiment of the present invention may modify the smart CIS pixel array 100 of FIG. 4 or the WTA circuit 200 of FIG. 9 to perform the "shrink" and "expand" function at a pixel level of an embodiment of the present invention so that the WTA circuit 200 locates a center of the pupil while the smart CIS pixel array shrinks and expands the image of the pupil. Further, when the number of the black pixels is less than a predetermined number (stop criterion circuit) the WTA circuit 200 may apply the identified central position of the pupil to the LSR.

Figure 10:
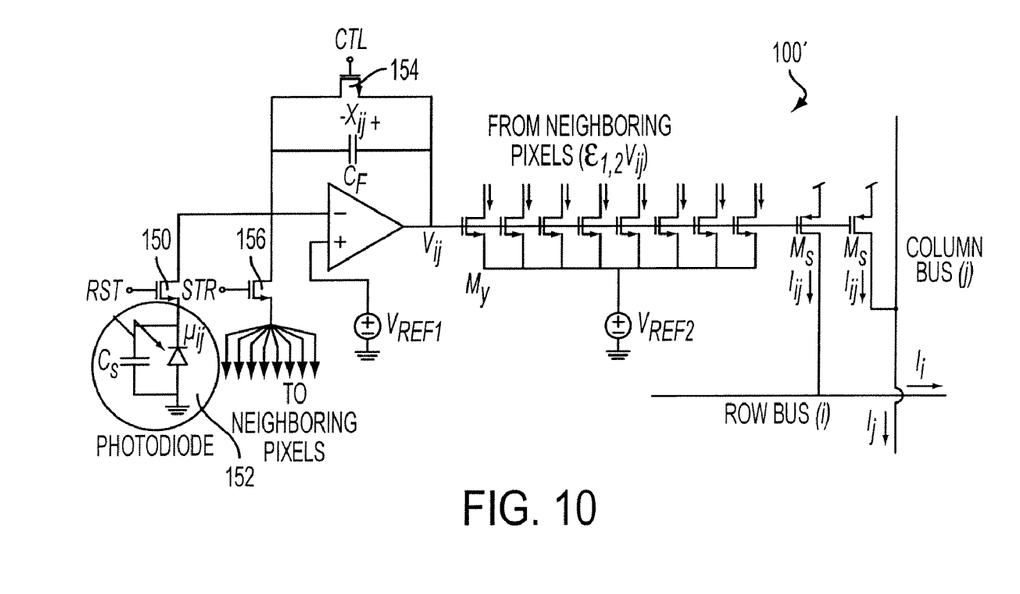
FIG. 10 shows an exemplary modified embodiment of a smart CIS pixel array circuit, according to an embodiment of the present invention.

An example of a circuit diagram of such a smart CIS pixel array 100' is shown in FIG. 10, according to an embodiment of the present invention. An RST transistor 150 serves to decide pre-charge and integration mode, and a CTL transistor 154 acts to discharge a feedback capacitor $C_F$. An STR transistor 156 decides whether or not pixels around a corresponding pixel is subjected to a feedback process. In the operation of the pixels, one cycle is divided into four periods as shown in FIG. 5. First, at a $T_{RST}$ period, a photodiode parasitic capacitor $C_S$ is pre-charged to a reference voltage $V_{REF1}$, and $C_F$ is reset. Since the state voltage $C_S$ of the pixel is $V_{REF1}$, which is smaller than $V_{REF1}+VT$ (a threshold voltage of the transistor), eight feedback transistors are all turned off so that any feedback is applied to surrounding pixels. At a next $T_{PHOTO}$ period, an RST transistor is turned off and $C_F$ is discharged to $(V_{REF1}-V_P)$. Here, $V_P$ is proportional to the intensity of light entering the pixel. At a last $T_{TX}$ and $T_{SRK}$, a CTR transistor is turned off, and the RST transistor is turned on while charges of $C_S$ is transferred to $C_F$. Then, the voltage of $V_X$ raises to $(V_{REF1}+V_{P*}C_F/C_F)$ and becomes higher than $(V_{REF2}+V_T)$ so that the eight feedback transistors are all turned on, and hence a corresponding feedback is applied to surrounding pixels. At this time, the state voltage is outputted as current by $M_R$ and $M_C$ transistors and then summed on a row-wise basis and a column-wise basis. When the STR transistor is turned on, the inter-pixel dynamics start.

Figure 11:
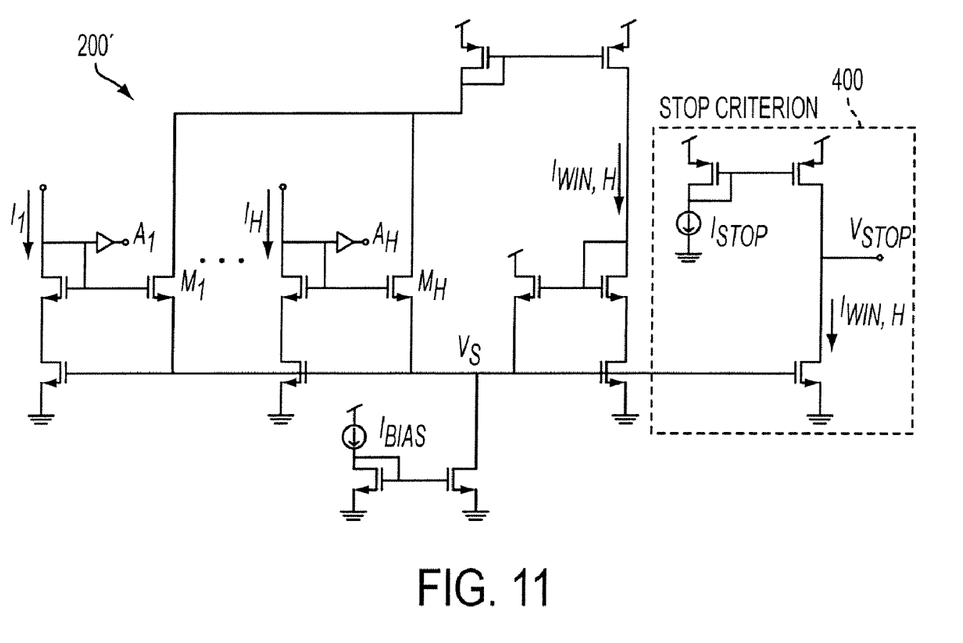
FIG. 11 shows an exemplary modified embodiment of a WTA circuit, according to an embodiment of the present invention.

Another example of the WTA circuit positioned in each row and column is shown in FIG. 11, according to an embodiment of the present invention. Referring to FIG. 11, a common source voltage $V_S$ of $M_{1, \ldots, N}$ transistors is set such that only a transistor having the largest one of input currents is turned on and the remaining transistors are all turned off. For the voltage of $A_{1, \ldots, N}$ nodes, only the voltage of the turned on transistor becomes high, and hence it is transferred to an input of the encoder. Then, the largest input current $I_{WIN}$ and a reference current $I_{STOP}$ are compared with each other. If the current $I_{WIN}$ is smaller than the reference current $I_{STOP}$, the address latching is performed.

Figure 12:
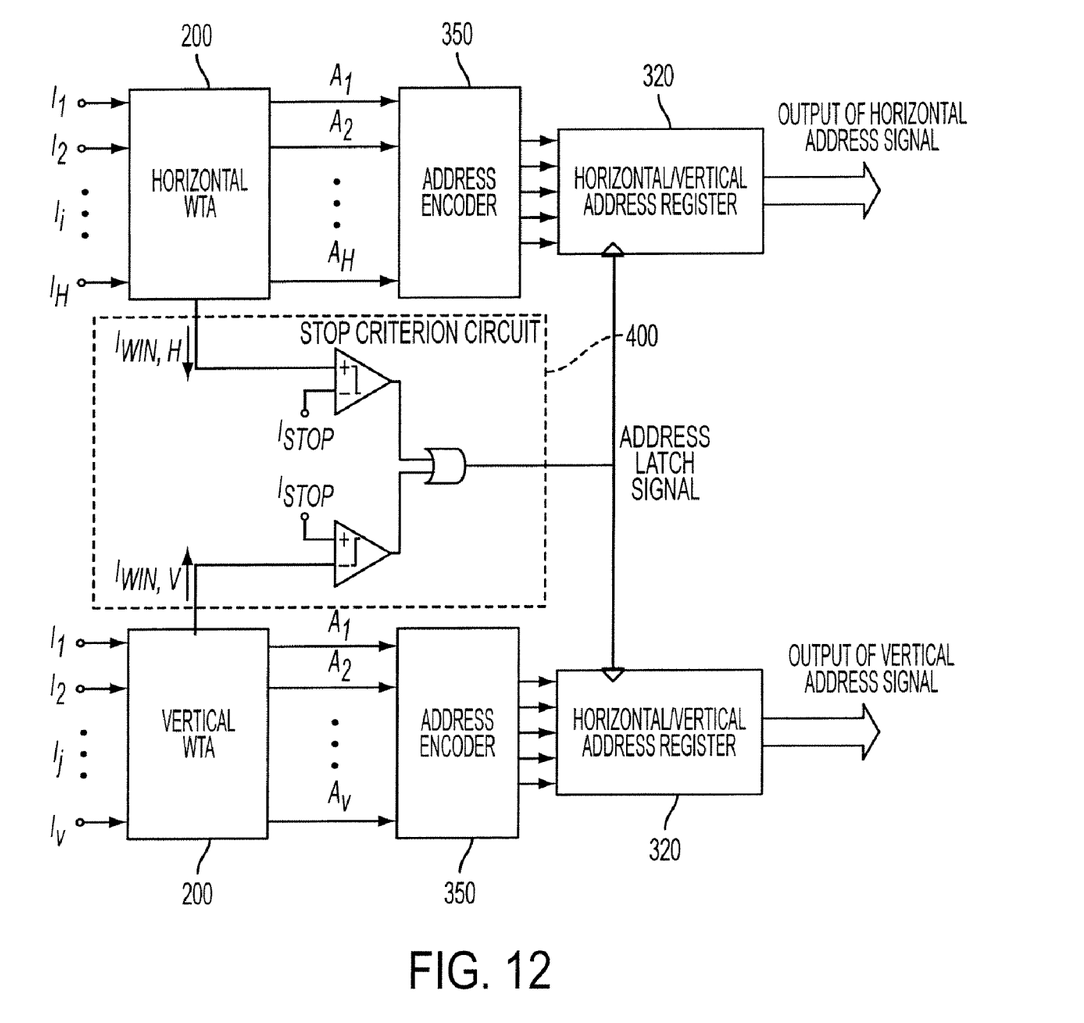
FIG. 12 illustrates an example of a position coordinate output using an address encoder, according to an embodiment of the present invention.

An embodiment of the present invention may also modify the circuit so as to store and output the coordinates of a position at which a user views, using a register or an encoder of different kind from that of the LSR. The operation of the address encoder circuit will be described with reference to FIG. 12, according to an embodiment of the present invention. The WTA 200' of FIG. 11 identifies location of a row (and/or a column) having the highest current value in each row (and/or column) of the CIS pixel array while existing in the row and column one by one, e.g., the location of a row (and/or column) having a greatest number of black pixels, and applies a signal indicating the identified location to the encoder 350. And, the stop criterion circuit 400 may compare the highest current value $I_{WIN}$ of the input values with a reference current value $I_{STOP}$, and generates a latching signal for application to the address register 320 if $I_{WIN}$ is lower than $I_{STOP}$, as shown in FIG. 12, so that address register 320 outputs digital data from the encoder 350 as a final output.

Additional variations in circuitry and/or other hardware may be realized according to the various aspects of the present invention.

As apparent from the foregoing, the methodology of finding the position of the center of the pupil is generally implemented through the software-based image processing using the DSP, but the spirit of the present invention does not exclude the fact that the inventive eye tracking method may be implemented with a hardware-based circuit. The technical scope or the right scope of the present invention is determined by a rational interpretation of the appended claims, but not limited by the particular illustrative embodiments.

The eye tracking system may be implemented in various applications, such as HMD, where the demand for HMD is high for military, video game and other interactive applications. A basic requirement of an advanced-level HMD is that the movement of the pupil is detected to display an image corresponding to the pupil movement. In the case where a traditional eye tracker is employed in a HMD, several peripheral devices such as a CCD camera, an ADC, a DSP chip and other devices are necessary. The use of peripheral devices results in a high consumption of power and restriction in movement. However, since the inventive eye tracker device of an embodiment of the present invention may be realized within a single chip, the addition of a display device enables the HMD to be easily implemented. Further the eye tracker of an embodiment of the present invention may be applied to various applications.

In case of the conventional eye tracker, the fabrication processes for CCD cameras, ADC and DSP chips require different processes thereby contributing to the implementation costs. However, in case of the inventive CIS (CMOS image sensor), a standard CMOS process may be employed for the CIS so that circuit integration for processing an analog signal, a digital signal and a mixed signal may be efficiently achieved for an integrated chip. Accordingly, the manufacturing cost is reduced to provide a highly technical commercialized product. In addition, the CIS pixel array of an embodiment of the present invention may be used to locate the center of the pupil of the eyes as well as enable the image processing process in a short time period. The application of the CIS pixel array may implement an iris recognition system, a fingerprint recognition system, etc., with a single chip so as to achieve wide spread commercialization.

The various embodiments of the present invention may be applied to many different scenarios. As discussed above, an eye tracker integrated chip may function as a pointing and/or input mechanism in connection with various devices. For example, the eye tracker integrated chip may be attached to an HMD, eyeglasses, an eye piece, a headset and/or other mechanism positioned at a close proximity to a user's eye, eyes or eye area. A receiving device may include eye sensor software for receiving a signal from the eye tracker integrated chip. In addition, the receiving device may be configured to receive a signal from the eye tracker integrated chip. For example, the receiving device may include a computer, a terminal, machinery, a display and/or other device that receives an input.

According to an exemplary application, a user may input specific information, such as a PIN, password, code or other sensitive information, to a receiving device, such as a terminal (e.g., ATM, etc.), using an embodiment of the present invention. A user may use an embodiment of the present invention to input data to a computer. For example, the user may control a cursor, in a similar manner as a mouse or other input device, with an embodiment of the present invention. In addition, the user may input keystrokes through the eye tracker of an embodiment of the present invention. The keyboard or an electronic keyboard may receive signals from the eye tracker integrated chip. In addition, the eye tracker of an embodiment of the present invention may be used in connection with opening, closing, locking, unlocking or performing other similar actions in connection with a door, vehicle and/or other structure. For example, the eye tracker may be used to input a code for unlocking or locking a car door, house door, safety deposit box, for example, and may effectively replace the use of a key or other similar mechanism.

According to the various embodiments of the present invention, the user may use the eye tracker alone or with manual inputs. For example, at an ATM machine, the user may enter a series of numbers or characters using the eye tracker and manually selecting the "enter" or similar key to accept each entered number or character.

An embodiment of the present invention may also control devices, such as a wheel chair, machinery, GPS component, vehicle, television, camera, PDA, cell phone and/or device. For example, the eye tracker integrated chip may be useful to handicapped or injured user's who are unable to use their hands to activate or control devices. For example, a user with limited use of his or her hands may use the eye tracker to control a wheel chair or other transportation device. The eye tracker of an embodiment of the present invention may also enable the user to interact with other devices as well. In addition, the eye tracker device may be useful for users who are temporary restricted in hand movement, such as while a user is driving or operating machinery. For example, the eye tracker device may enable a user to interact with a GPS system, while keeping both hands on the steering wheel.

In addition, the eye tracker of an embodiment of the present invention may be used to control devices through a remote control. For example, the user may control an un-manned vehicle through a remote control operated by the eye tracker. Other devices that may be remotely controlled may include other un-manned vehicles, robots, cars, trains, buses, trucks, and/or other devices.

According to another example, the user may interact with software, such as video games, training programs, tutorials and/or other interactive software. Another application for the various embodiments of the present invention may apply to simulators. For example, a user may interact with a simulator for honing a desired skill in a field, such as shooting, archery, baseball, golf, and/or other activity. For a virtual simulator directed to pitching a baseball, an embodiment of the present invention may be used to store a pitcher's intended target as identified by the eye tracker device. By establishing a relationship between the user's intended target, as identified by the target the user is viewing, and the actual position of the ball thrown, the user is able to improve the accuracy of pitching a ball in a strike zone, for example. Similar relationships may be established for other simulators that involve accuracy.

An embodiment of the present invention may be used to verify a user's identity through an output of the eye tracker device. The eye tracker device may be used to identify an individual based on certain unique features of the user's eye image, which may involve a combination of size, shape, movement, color and/or other quality of the individual's eye(s). For example, when an individual wants to enter a room, the individual may look at the eye tracker device that may be positioned at an entrance area. The eye tracker device may evaluate the characteristics of the individual's eye image or images and may either accept or deny the entrance. The CIS pixel array of an embodiment of the present invention may implement an iris recognition system and/or other recognition system (e.g., a finger-print recognition system, etc.) within a single chip for a wide variety of different applications.

An embodiment of the present invention may be used to detect a state of the user's eye, such as when the user's eye is closed for a period of time. This application may be useful to detect when the user has fallen asleep or is about to fall asleep while the user is driving. In this example, an alarm or other trigger may be activated to wake the user and prevent an accident. The eye tracker may detect eye movement in general where a certain amount (or lack) of movement may be indicative of the user's state of health.

In addition, the eye tracker may be used to control an action from a device. An embodiment of the present invention may be used in a weapons or training application. For example, the eye tracker may be used to control the firing of a weapon. An exemplary application may involve when a user views a target, the corresponding weapon may fire in the direction that the user is viewing. This may occur while the user is operating a machine with an attached weapon, where the aiming of that weapon is controlled by the eye tracker.

Another application of the eye tracker may include the medical field. For example, in the laser eye surgery, the damage to the pupil of an eye may be essentially prevented. The eye tracking device may monitor or identify a position of the pupil of the eye, the tracked information may be received by a device that controls the direction of the laser and configured so that the laser would not be permitted to be pointed at the pupil at any instance.

Another application may involve an eye tracking solution for research applications. The ability to measure and analyze eye movements during visual stimulation may be important for the new areas of research conducted using functional Magnetic Resonance Imaging (fMRI). Monitoring a subject's eye movements and gaze positions during a visual stimulation may allow an objective assessment of experiments. Analysis of eye movements may be desired to understand cognitive and neural processes of a healthy individual, along with unhealthy individuals. These applications may involve eye tracking solutions adapted to the unique constraints of the magnet, the stimulus setup, and the general requirements of the fMRI setting.

The eye tracking device of an embodiment of the present invention may be integrated into vehicles to study driver behavior and improve the interior design of a vehicle. Due to the modular and portable structure of the eye tracking device, minor change may be implemented to apply to the standard configuration. Additional devices are not required to capture the driver's gaze path. The system may be easily calibrated inside the vehicle or by using outside targets. An optional sunlight tolerant eye tracking software may improve the results under extreme conditions where external and/or changing infrared artifacts are present.

The present invention is not to be limited in scope by the specific embodiments described herein. Indeed, various modifications of the present invention, in addition to those described herein, will be apparent to those of ordinary skill in the art from the foregoing description and accompanying drawings. Thus, such modifications are intended to fall within the scope of the following appended claims. Further, although the present invention has been described herein in the context of a particular implementation in a particular environment for a particular purpose, those of ordinary skill in the art will recognize that its usefulness is not limited thereto and that the present invention can be beneficially implemented in any number of environments for any number of purposes. Accordingly, the claims set forth below should be construed in view of the full breath and spirit of the present invention as disclosed herein.

The invention claimed is:

1. An integrated chip for detecting eye movement, the integrated chip comprising:
    a sensor component for receiving an image of a user's eye and processing the eye image to identify a center of a pupil of the eye image; wherein the sensor component comprises a CMOS image sensor (CIS) pixel array,
    wherein the CIS pixel array comprises:
    a shrink means for reducing a dark interference region around a pupil portion of the eye's image; and
    an expand means for reducing a light interference region occurring in the pupil portion of the eye's image,
    wherein the CIS pixel array identifies a center of the pupil of the eye image at a pixel level by shrinking the eye image toward the center of the pupil where the center of the pupil identifies a point the user is viewing.

2. The integrated chip of claim 1, wherein the shrink means reduces the dark interference region by convening a plurality of dark pixels of the dark interference region to a plurality of white pixels to locate a center of the pupil.

3. The integrated chip of claim 1, wherein the expand means reduces the light interference region caused by a light source or external source.

4. The integrated chip of claim 1, wherein the CIS pixel array comprises a M×N cellular neural network having M columns and N rows, where each pixel of the CIS pixel array outputs a current state value where each corresponding current state value for each pixel is summed for a plurality of rows and columns.

5. The integrated chip of claim 4, wherein the each pixel of the CIS pixel array comprises a photodiode, where an output voltage of the photodiode is changed depending on brightness of light.

6. The integrated chip of claim 1, further comprising:
    a plurality of winner-take-all (WTA) circuits connected to a plurality of rows and columns of the CIS pixel array for identifying a location of a row and a column having a highest current value in the row and column and generating an output signal indicative of the identified location; and
    a plurality of loadable shift registers (LSRs) connected to the plurality of WTA circuits for receiving the output signal, storing the received output signal and outputting the stored output signal though a shift operation.

7. The integrated chip of claim 1, further comprising:
    a plurality of winner-take-all (WTA) circuits connected to a plurality of rows and columns of the CIS pixel array for identifying a location of a row and a column having a highest current value and generating an output signal indicative of identified location; and
    a plurality of encoders connected to the plurality of WTA circuits for receiving the output signal to encode the received output signal and outputting the encoded signal.

8. The integrated chip of claim 6, further comprising
    a stop criterion circuit connected to the plurality of WTA circuits and the plurality of LSRs for receiving the output signal and generating a LSR latch signal so that when a number of black pixels of the row and column of the CIS pixel array is less than a predetermined number, the location of the row and column is stored in the LSR.

9. The integrated chip of claim 8, wherein the predetermined number of the black pixels is two.

10. The integrated chip of claim 8, wherein the stop criterion circuit compares a highest current value $I_{WIN,h}$ and $I_{WIN,V}$ of the input signals of the row and column with a reference current value $I_{STOP}$ and generates a latching signal for application to the LSRs if $I_{WIN,h}$ and $I_{WIN,V}$ are lower than $I_{STOP}$, respectively, wherein the LSRs outputs digital data.

11. A semiconductor integrated circuit in which the integrated chip of claim 1 is manufactured by a well-known semiconductor integration technique.

12. A system comprising the integrated chip of claim 1, wherein the integrated chip is in communication with a receiving device configured to receive an output from the integrated chip for identifying the point the user is viewing on the receiving device.

13. The system of claim 12, wherein the point the user is viewing is a target in a training simulator.

14. The system of claim 13, wherein the training simulator identifies the target viewed by the user and an actual target of the training simulator and wherein the target viewed by the user and the actual target are compared.

15. The system of claim 12, wherein the point the user is viewing is a target in an interactive game application.

16. The system of claim 12, wherein a direction that the receiving device is positioned is controlled by the output.

17. The system of claim 16, wherein an action of the receiving device is further controlled by another output of the integrated chip.

18. The system of claim 12, wherein one or more characteristics of the eye image are determined.

19. The system of claim 18, wherein the user's identity is determined by the one or more characteristics of the eye image.

20. The system of claim 12, wherein the receiving device is a laser device used in eye laser surgery wherein the laser device is configured to avoid a predetermined area of the eye.

21. The system of claim 12, wherein the receiving device is a transportation device that is configured to receive the point the user is viewing as input to control the transportation device.

22. The system of claim 21, wherein the transportation device is one of a vehicle and a wheelchair.

23. The system of claim 12, wherein the point the user is viewing identifies a security code for entry to the receiving device.

24. The system of claim 23, wherein the receiving device is an automated teller machine.

25. The system of claim 12, wherein the point the user is viewing is received as input to a component within a vehicle.

26. The system of claim 25, wherein the component within the vehicle is a global positioning system.

27. The system of claim 12, wherein the integrated chip is connected to an eye piece positioned at a close proximity to a user's eye area.

28. A method for implementing an integrated chip for detecting eye movement, wherein the integrated chip comprises an image sensor component for receiving an eye image and processing the eye image to identify a center of a pupil of the eye, the method comprising the steps of:
receiving an eye image by the image sensor;
identifying an interference in the eye image;
removing the interference in the eye image, wherein the step of removing interference comprises at least one of a shrink function for removing a dark interference region around the pupil of the eye image by modifying a plurality of dark pixels into white pixels and an expand function for removing a light interference region in the pupil of the eye image; and
locating a center of a pupil of the eye image at a pixel level by shrinking the eye image toward the center of the pupil where the center of the pupil identifies a point the user is viewing.

29. The method of claim 28, further comprising the steps of:
outputting a current state value of each pixel of a CIS pixel array that corresponds to one or more of light and shade wherein the corresponding current values are summed for the rows and columns of the CIS pixel array;
identifying a location of row and column having a highest current value in the CIS pixel array and
outputting a signal indicative of the location of the row and column to a receiving device.

30. The method of claim 29, wherein the step of outputting further comprises the steps of:
comparing the highest current value $I_{WIN,h}$ and $I_{WIN,V}$ of input signals of the row and column with a reference current value $I_{STOP}$; and
generating digital data as an output if $I_{WIN,h}$ and $I_{WIN,V}$ are lower than $I_{STOP}$.

* * * * *